United States Patent
van Kalken et al.

(10) Patent No.: US 9,777,383 B2
(45) Date of Patent: Oct. 3, 2017

(54) CELL AND SYSTEM FOR PREPARATION OF ANTIMICROBIAL SOLUTIONS

(71) Applicant: Clarentis Holding, Inc., Palm Beach Gardens, FL (US)

(72) Inventors: Duke van Kalken, Palm Beach Gardens, FL (US); Nathan Waldner, Manitoba (CA)

(73) Assignee: CLARENTIS HOLDING, INC., Palm Beach Gardens, FL (US)

(*) Notice: Subject to any disclaimer, the term of this patent is extended or adjusted under 35 U.S.C. 154(b) by 0 days.

(21) Appl. No.: 15/162,076

(22) Filed: May 23, 2016

(65) Prior Publication Data

US 2016/0265123 A1   Sep. 15, 2016

Related U.S. Application Data

(60) Continuation-in-part of application No. 14/694,334, filed on Apr. 23, 2015, now Pat. No. 9,347,140,
(Continued)

(51) Int. Cl.
| | |
|---|---|
| *C25B 1/26* | (2006.01) |
| *C25B 9/04* | (2006.01) |
| *C25B 11/08* | (2006.01) |
| *C02F 1/467* | (2006.01) |
| *C25B 15/02* | (2006.01) |
| *C25B 1/22* | (2006.01) |

(Continued)

(52) U.S. Cl.
CPC .............. *C25B 15/02* (2013.01); *A01N 59/00* (2013.01); *C01B 11/04* (2013.01); *C02F 1/4674* (2013.01);
(Continued)

(58) Field of Classification Search
None
See application file for complete search history.

(56) References Cited

U.S. PATENT DOCUMENTS 3,439,080 A * 4/1969 Cervenka ............... C25B 9/04
                                                    264/105
3,748,250 A * 7/1973 Schmidt et al. ....... C25B 11/02
                                                    204/252
(Continued)

OTHER PUBLICATIONS

Duval, D.J. et al., Chapter 2 Mullite, *Ceramic and Glass Materials: Structure, Properties and Processing*, Shackelford, J.; Doremus, R.H. (Eds.), Springer, 2008, pp. 27-39.
(Continued)

*Primary Examiner* — Brian W Cohen
(74) *Attorney, Agent, or Firm* — Saliwanchik, Lloyd & Eisenschenk (57) ABSTRACT

A system to prepare an antimicrobial solution by the electrolysis of brine is presented where the antimicrobial solution is a solution comprising HOCl that contains a HOCl concentration in excess of 500 ppm or more at a pH of 6 to 6.8 with a low residual salt concentration and displays a stability in excess of 60 days and can have a HOCl concentration in excess of 450 for 180 days. The system includes an electrolysis cell that is improved by a superior anode and ceramic membrane such that when employed with a DC power supply controlled by a microprocessor and a controlled brine concentration provided to the cell at ambient temperature at a controlled rate, delivers a fluid that is continuously monitored by a pH probe and an ORP probe for input to the microprocessor.

14 Claims, 4 Drawing Sheets

Related U.S. Application Data which is a division of application No. 13/092,653, filed on Apr. 22, 2011, now abandoned, which is a continuation-in-part of application No. PCT/US2011/020691, filed on Jan. 10, 2011.

(60) Provisional application No. 61/293,467, filed on Jan. 8, 2010.

(51) Int. Cl.

| | | |
|---|---|---|
| *C25B 15/08* | (2006.01) | |
| *C25B 9/08* | (2006.01) | |
| *A01N 59/00* | (2006.01) | |
| *C01B 11/04* | (2006.01) | |
| *C02F 1/00* | (2006.01) | |
| *C02F 1/461* | (2006.01) | |

(52) U.S. Cl.
CPC ............... *C25B 1/22* (2013.01); *C25B 1/26* (2013.01); *C25B 9/04* (2013.01); *C25B 9/08* (2013.01); *C25B 15/08* (2013.01); *C02F 1/001* (2013.01); *C02F 2001/46138* (2013.01); *C02F 2201/46135* (2013.01); *C02F 2201/46145* (2013.01); *C02F 2209/005* (2013.01); *C02F 2209/04* (2013.01); *C02F 2209/06* (2013.01); *C02F 2209/40* (2013.01)

(56) References Cited

U.S. PATENT DOCUMENTS

| | | | |
|---|---|---|---|
| 3,819,329 A | | 6/1974 | Kaestner et al. |
| 4,240,884 A | | 12/1980 | Pellegri |
| 4,532,018 A | | 7/1985 | Wright et al. |
| 4,857,158 A | | 8/1989 | Cawlfield |
| 4,952,298 A | | 8/1990 | Bouche-Pillon et al. |
| 5,932,171 A | | 8/1999 | Malchesky |
| 5,958,229 A | * | 9/1999 | Filiopoulos ........ B01D 19/0068 204/278 |
| 6,235,167 B1 | | 5/2001 | Stauffer |
| 6,426,066 B1 | * | 7/2002 | Najafi ................ A61K 33/14 424/613 |
| 6,632,347 B1 | | 10/2003 | Buckley et al. |
| 6,719,891 B2 | | 4/2004 | Ruhr et al. |
| 6,998,057 B2 | | 2/2006 | Ferguson et al. |
| 7,374,645 B2 | * | 5/2008 | Davis ................. C25B 9/08 204/242 |
| 7,691,249 B2 | * | 4/2010 | Daly ................. C02F 1/46104 205/100 |
| 2005/0183949 A1 | | 8/2005 | Daly et al. |
| 2006/0054510 A1 | | 3/2006 | Salerno |
| 2007/0045105 A1 | * | 3/2007 | Schussler ............ C25B 1/46 204/230.2 |
| 2008/0200355 A1 | | 8/2008 | Emmons |
| 2010/0283169 A1 | * | 11/2010 | Emmons ............ C04B 35/04 264/43 |
| 2011/0226615 A1 | * | 9/2011 | Bakhir ................ C25B 9/08 204/252 |
| 2011/0256243 A1 | * | 10/2011 | Van Kalken ........ A01N 59/00 424/661 |

OTHER PUBLICATIONS

Wahl, F.M et al., Phase Transformations in Silica-Alumina Mixtures as Examined by Continuous X-Ray Diffraction, *The American Mineralogist*, Sep.-Oct. 1961, pp. 1064-1076, vol. 46.

* cited by examiner

*Figure 4* ized. Systems that produce near neutral aqueous solutions are known and marketed; however, these systems produce solutions of limited stability where insufficient concentrations of hypochlorous acid HOCl are produced to allow the use of the resulting solution as an effective antimicrobial solution.

US 9,777,383 B2

CELL AND SYSTEM FOR PREPARATION OF ANTIMICROBIAL SOLUTIONS

CROSS-REFERENCE TO RELATED APPLICATIONS

This application is a continuation-in-part of U.S. Ser. No. 14/694,334, filed Apr. 23, 2015, which is a divisional of U.S. Ser. No. 13/092,653, filed on Apr. 22, 2011, which is a continuation-in-part of International Patent Application No. PCT/US2011/020691, filed Jan. 10, 2011, which claims the benefit of U.S. Provisional Patent Application Ser. No. 61/293,467, filed Jan. 8, 2010, the disclosures of which are hereby incorporated by reference in their entirety, including any figures, tables, or drawings.

BACKGROUND OF THE INVENTION

The electrochemical generation of disinfective aqueous solutions has been studied for many years and many small scale devices have been designed. Unfortunately, such systems have had little market penetration because devices have typically proven to be unreliable and of relatively poor quality. Furthermore, the available systems do not provide solutions that display a sufficiently constant output quality, such that quality control requirements can be achieved and verified. Systems that produce near neutral aqueous solutions are known and marketed; however, these systems produce solutions of limited stability where insufficient concentrations of hypochlorous acid HOCl are produced to allow the use of the resulting solution as an effective antimicrobial solution.

BRIEF SUMMARY OF THE INVENTION

Embodiments of the present invention are directed to a system of preparing nearly neutral (approximately pH 6.5) solutions comprising HOCl that have concentrations of HOCl in excess of 100 ppm such that they can be used as an antimicrobial. The system is designed to be energy efficient by using a digital DC power supply that is controlled by a microprocessor to impose a nearly constant current across the electrodes of an electrolysis cell with a relatively low floating voltage. The constant current, in conjunction with a controlled fluid composition (primarily brine concentration) and flow rate, is achieved by the microprocessor control of the voltage from the power supply. Microprocessor control of valve positions and pump rates in conjunction with the constant current permits the generation of a consistent solution comprising HOCl as indicated by oxidation/reduction potential (ORP) and pH probes situated in the effluent stream. The electrolysis cell includes end-caps that position and seal cylindrical electrodes and a cylindrical porous membrane situated between the electrodes. The anode is manufactured using a process to apply a coating on the anode. In addition, the tab on the anode has been modified based on the surface area of the anode to allow for a better distribution of power on the anode and to protect the coating of the anode. The system is designed to segregate solutions comprising HOCl that achieves the set values of ORP and pH measured at the probes from solutions that are outside of the specification and from solutions used to clean the system. The system can allow the determination of degradation of the system using the programmed microprocessor where the system is automatically taken out of the production mode and placed in a cleaning mode and subsequently returned to the production mode as needed. By attaining and maintaining a desired constant cell conductance, brine solution feed concentration, and HOCl solution of a prescribed pH and conductivity, an antimicrobial solution that can be relatively high in HOCl yet display superior stability and shelf-life is achieved.

Another embodiment of the invention is directed to the preparation of a solution comprising HOCl of more than 100 ppm HOCl, for example 500 to 1,000 ppm HOCl, or more, with a pH of 6.0 to 6.8 at a rate in excess of 50 L/hr. The method involves the use of the above system that uses microprocessor controlled electrolysis of a brine solution, such that the pH is constantly monitored and adjusted to achieve the desired HOCl solution.

Another embodiment of the invention is directed to an electrolysis produced solution comprising HOCl, where the HOCl concentration is in excess of 100 ppm and the NaCl concentration is low where cations other than $H^+$, which exists as $H_3O^+$ ions in water, and $Na^+$ do not produce a conductance value of more than 15 mS. The HOCl solution having this composition is an excellent antimicrobial agent where the solution is stable for an extended period of time after production, well in excess of other HOCl solutions prepared using presently available electrolysis systems.

DETAILED DESCRIPTION OF THE INVENTION

Embodiments of the invention are directed to a system for the manufacture of antimicrobial electrolyte solutions comprising hypochlorous acid (HOCl) for use as a bactericide, viricide and/or sporicide. The antimicrobial electrolyte solutions comprising hypochlorous acid (HOCl) can also be used where the oxidation of chemical compounds in addition to, or alternatively to, antimicrobial action is required. For example, in industries such as the oil and gas industry, the antimicrobial electrolyte solutions will reduce or eliminate hydrogen sulfide, biofilm, and biomass, in addition to microbes when used for well, storage tanks, or pipeline treatment.

The system can employ one or more electrolysis cells. Electrolysis cells, as disclosed in U.S. Pat. No. 7,374,645 or U.S. Pat. No. 7,691,249, both of which are incorporated herein by reference, can be modified. A compression sealable electrolysis cell assembly, according to an embodiment of the invention is employed with the exemplary system as disclosed herein. The cell assembly shares common features with those disclosed in U.S. Pat. No. 7,374,645, having two insulating end pieces, each having three concentric seats to position and seal an exterior anode tube, an interior cathode tube and a central ceramic membrane tube that separates the anode from the cathode. The assembly can employ, but does not require, one or more rods to compress the assembly; as the compression can be performed mechanically and the assembly fixed by other mechanical means, including, but not limited to, bolts through the end pieces and one or more electrodes, threaded electrodes with matching threaded end pieces, or compressed and secured with an adhesive resin. The central seat is sealed to the ceramic tube using one or more O-rings, gaskets, or compressible ridges in the end piece one or more holes parallel to the central axis of the concentric seats. The ceramic membrane tube has a length that is less than the length of the anode such that when the anode is seated with the two end pieces and the assembly sealed the anode does not allow force to be applied to the ceramic tube when sealed. Each end piece has two ports which end in fittings. The exterior port from each end piece addresses an anode chamber, which is a sealed volume defined by the anode and exterior of the ceramic membrane tube. The interior port from each end piece addresses a cathode chamber, which is a sealed volume defined by the cathode and interior of the ceramic membrane tube.

The compression sealable electrolysis cell assembly is improved over that of U.S. Pat. Nos. 7,374,645 and 7,691,249 in that the ceramic membrane tube is an injection molded ceramic membrane tube, such that the cracks and other defects that form by machining or by compression molding are avoided and such that the tube thickness can be uniform with a variance in thickness of less than one percent over the entire length of the ceramic membrane tube. The compression sealable electrolysis cell assembly, according to an embodiment of the invention, can be constructed without compression forced by rods, but can be applied by other means, including, but not limited to, connection to the side of one or both electrodes or the use of an external vice type structure to provide compression after or during the fixing of the cell. An adhesive can be employed to additionally fix and/or seal the cell. The anode is a titanium tube with a catalytic coating over at least its interior surface, where the catalytic coating comprises a RoHS compliant multiplicity of platinum group metal oxides selected from: ruthenium; rhodium; palladium; osmium; iridium; and platinum oxides, for example, but not limited to, the three or more oxides that can be a mixture of ruthenium, palladium, and iridium oxides. The catalytic coating of this anode promotes chloride oxidation over oxygen formation from water. The electrical connectors (taps) employed can be situated through the end caps or can be situated on any other portion of the electrodes. Particularly in the case of the anode, the electrical connector can have a relatively large surface area, for example, 1.5 to 5 percent of the outer cylindrical surface of the anode, to promote cooling of the connection, which otherwise results in heating that limits the voltage that can be applied to the cell, which is detrimental to the quality of the antimicrobial fluids produced and to the usable lifetime of the anode. By employing the improvements to the anode and ceramic membrane tube, the efficiency of chloride oxidation is significantly improved such that NaCl concentrations employed can be significantly decreased to yield high stability of relatively concentrated HOCl solutions that are produced by the system.

Because of the size increase of the cell's electrical connections to electrodes, particularly the size of the connection to the anode, an increase of the current density to as high as 250 A/in$^2$ can be used with air cooling of the connection avoiding significant localized heating and oxidation of the connection. The size of the connection (tap) on the anode of the cell is advantageously large for the surface area of the anode allowing a very uniform application of the current to the anode and improving cell stability and electrode lifetime. The larger tap distributes heat more evenly over the electrode surface, resulting in less wear on the coating of the anode, The tap can be situated on any portion of the anode, for example, but not limited to, the center of the anode or through the end cap on the end of the anode.

The electrolysis cell employs a uniform ceramic membrane situated between the electrodes and is essentially free of cracks and other defects. The nearly defect free uniform ceramic membrane is achieved by injection molding of the ceramic membrane tube and finishing in a manner that does not strain the tube significantly. For example, an injection molded membrane tube can comprise 85 to 90% alumina and 7 to 9% silica, for example, but not limited to, 87% alumina and 8% silica. The membrane tube can be formed and finished with a thickness of about 5 to 7 mm, for example, 6 mm, with a tube thickness variance of about 2% or less and posses about 0.3 μm pores.

Absent the larger tap, the mixed metal oxide coating including a blend of platinum group metal oxides on the anode, and the improved ceramic membrane, the formation of HOCl is limited to about 400 ppm unless a NaCl concentration in excess of 7 g/L, generally greater than 9 g/L, is employed with prior art electrolysis cells. For reference, salt concentrations in excess of 9, generally in excess of 12 g/L, are required for 500 ppm HOCL produced from the cell known as Fem-3, which is described in Bakhir et al., U.S. Pat. No. 5,427,667, and other common cells employed in the market. With the improved cells, at salt concentration of 3 to 4 g/L a very high salt conversion can be achieved such that HOCl solutions in excess of 1,000 ppm, or even 1400 ppm can be formed where a current of about 200 A or more is maintained, with production maintained at the high efficiency over long periods of time.

An unexpectedly much stronger, more stable and better controlled antimicrobial liquid is achieved by the system. The resulting improvement results due to a combination of factors, including having a high quality saturated brine fed at normal room temperature into the improved electrolytic cell, using a relatively thick alumina ceramic ion permeable membrane manufactured by injection molding and with its ends finished to tight specifications, a superior anode coating having a multiplicity of platinum group metal oxides, and an optimized tab to the anode that allow the maximum amount of power on the cell without premature passivating of the coating, that promotes the oxidation of chloride ions to HOCl while at the same time significantly reducing the production of $O_2$ from water electrolysis and results in a much lower residual salt conversion. A reduction in salt is essential for use of the HOCL solutions in agriculture, aquaculture, animal husbandry and food processing, and is highly advantageous for applications such as cooling towers and bio-film removal in water systems to minimize corrosion.

Although a high quality analog DC power supply can be employed, particularly with smaller electrolysis cells, it is advantageous to employ a nearly constant DC current from a digitally controlled power supply to the electrodes of the electrolysis cell. Analog-digital, and digital-analog DC power supplies can be used. This cell, equipped with the improved anode with a superior coating and the large tap, permits use for as much as 5,000 hours or more with a continuous series of working and cleaning cycles where the working cycle is, for example, approximately four times that of the cleaning cycles. The system can be adjusted to increase or decrease the periods of working and cleaning as needed. For example in a 24 hour period, the working period can be up to 20 hours. The improved cell and system allows the production of anolyte solutions with HOCl concentrations, for example, in excess of 100 ppm, and up to 1,400 ppm or more, where the electrical conductance of the solution does not exceed 15 mS as residual NaCl concentration is low, allowing the system to be used to generate antimicrobial fluids that can be used as sporicides. The catholyte solution that is cogenerated is a sodium hydroxide solution that can be used as a cleaning/degreaser and can be used in conjunction with the solution comprising HOCl for some applications, for example, some pharmaceutical applications.

Figure 1:
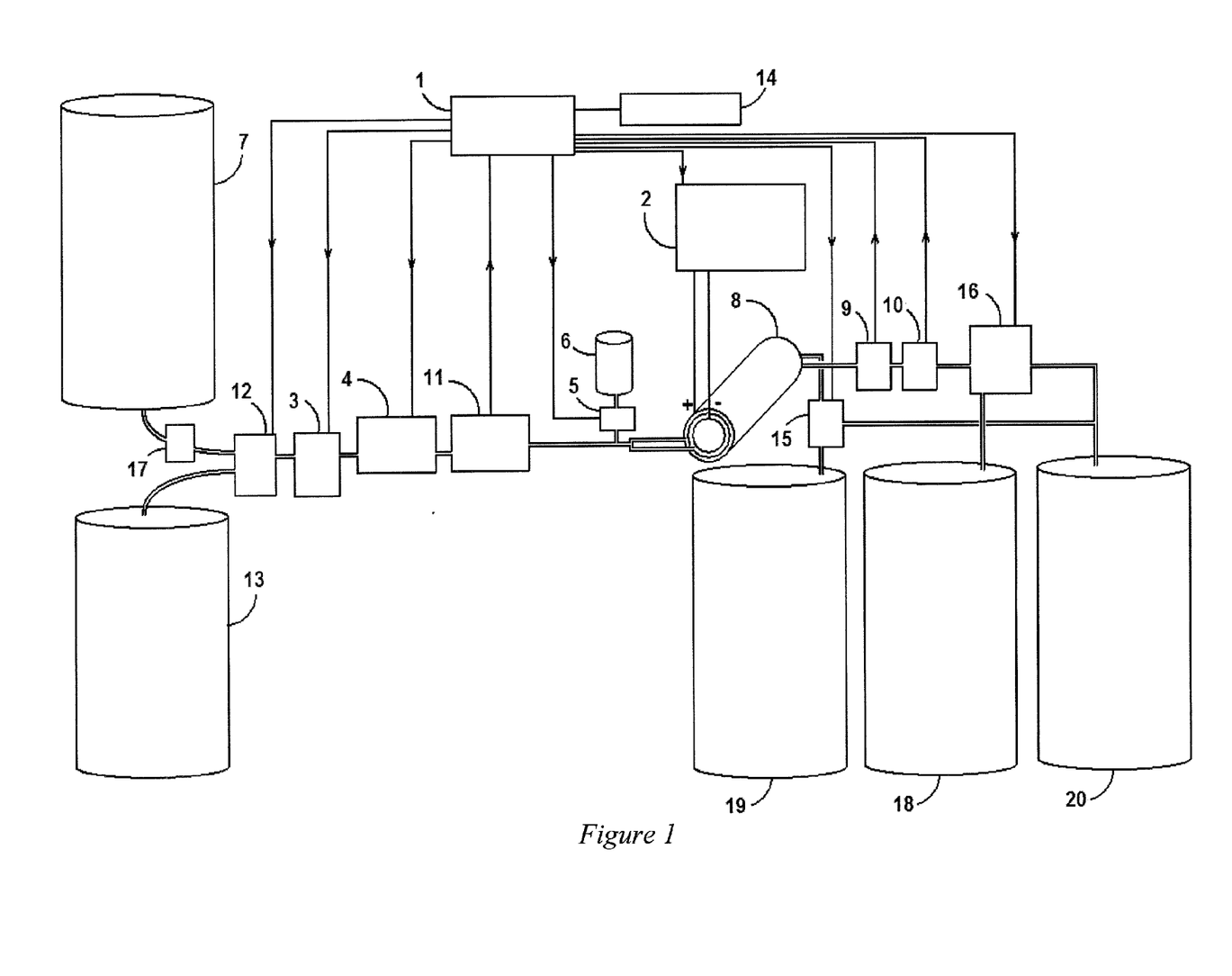
FIG. 1 is a schematic representation of an exemplary electrolysis system for the preparation of a solution comprising HOCl according to an embodiment of the invention where arrows indicate signal input or output to the microprocessor.

As illustrated schematically for an exemplary system, a microprocessor 1 is used to receive input signals of process and fluid parameters and to output signals to components to adjust system parameters. A data storage device can be connected to the microprocessor 1, for example, one or more memory cards or even a printed or plotted output, to record the consistency and quality of the solution produced and all events and values of parameters during a production run. The microprocessor 1 is used to control a digital DC power supply 2 to achieve a constant current. Advantageously, the use of the controlled digital power supply 2 allows for a significantly lower power consumption that is observed in all systems currently available and allows the cell to convert nearly all of the NaCl to HOCl leading to an enhanced stability of the resulting antimicrobial solutions. Alternatively, another alkali metal chloride, for example KCl can be used in place of NaCl brine. At least one metering pump 3 and/or flow controller 4 is used to feed aqueous brine to the electrolysis cell with a constant concentration at a controlled rate. Rather than using a stock brine solution, in an embodiment of the invention, a controlled pump 5 injects brine of a fixed concentration in a reservoir 6 into an incoming water supplied from a reservoir 7, or other source, such that a constant current is readily maintained at a preset value. Saturated brine can be maintained at a fixed concentration, as a saturated solution, by agitating the fluid of the reservoir 6 using a pump or a stirrer. Inline oxidation/reduction potential (ORP) 9 and pH 10 probes and flow meter(s) 11 are employed to provide input to the microprocessor 1 of the condition of the electrolyzed antimicrobial solution and the rate of its production. Software control allows the assessment of the input data and determines signal outputs to adjust the voltage of the power supply 2, the solution flow rate and/or the brine concentration such that desired ORP and pH values are achieved and maintained throughout the production period. Controlling the brine concentration and the DC current permits the production of a single stream of liquid that is an antimicrobial solution with a desired pH with a desired HOCl concentration. For example, the system can be set to provide an antimicrobial solution with a pH of 6.2 to 6.6, where an optimal level of HOCl is found in the solution. Lower and higher pH solutions can be achieved, where the pH can be for example from about 5.4 to about 6.8. An ORP of more than 800 mV is achieved with the system, according to an embodiment of the invention. The ability to tightly maintain pH, solution conductivity, current, flow rates, and brine concentration allows the formation of a HOCl solution that displays little loss in concentration over periods of 60 days or more, for example, 90 or even 120 days or more. A pH lower than 6 can occur upon storage, for example, a pH of as low as 5 can occur upon storage where the HOCL concentration can remain above about 500 ppm. An ORP of more than 800 mV is achieved with the system according to an embodiment of the invention.

The system can be designed to allow automated microprocessor controlled periodic cleaning of the cell. Valve(s) 12, 15, and 16 and pump(s) 3 are activated or deactivated to take the working cell 8 out of an antimicrobial fluid production mode and initiate a cleaning cycle, using a cleaning solution from a reservoir 13 for a period of time. For example, the system can cycle between a production orientation of, for example, four hours followed by a cleaning and cooling or resting cycle/orientation of, for example, one or more hours and continue such production for a period of up to six months, or even longer, without maintenance that requires the intervention of an operator to dissemble and reassemble the cell or other components of the system when appropriate pumps, filters and regulators are employed. The proportions of production time and cleaning time will vary with the quality of water that is introduced to the electrolysis system. The system can optionally include a sensor to verify when the cleaning process is complete, minimizing the amount of time that the system must be diverted from production of the antimicrobial solution.

The system according to embodiments of the invention includes a digital AC to DC power supply 2 where, for example, a single phase 220 V AC input is converted to DC voltages of up to 30 V, DC with a cell current of up to 65 A, which is controlled by a microprocessor. In other embodiments of the invention the DC voltage and amperage can be lesser or can be greater; for example, a large cell may require a current of 65 or even 100 A. In an embodiment of the invention, the AC input can be, for example, from a 208 V 3-phase power supply, which is advantageous for systems including large and multiple electrolysis cells 8. The microprocessor can be equipped with input and output, data monitoring 14 devices and, optionally, data storage anchor plotting components, including a visual display. The microprocessor 1 is controlled by software prepared for or adapted to the electrolysis system, and the microprocessor 1 can be remotely accessed to observe current parameters and readings and/or to modify production settings. The output can be stored and/or recorded to carry out quality control functions. Input of the ORP, pH, and flow values to the microprocessor 1 allow automatic adjustment of the DC voltage to maintain a constant current and achieve the desired HOCl concentration in the antimicrobial fluid, adjustment of the fluid flow rate, and to control the appropriate amount of brine entering the electrolysis cell 8 during production and cleaning solution, for example a muriatic acid solution, during cleaning of the system. The input is received from at least one ORP probe, at least one pH probe, and at least one flow indicator. A pressure regulator can be included in the system. A probe that determines the quality of the cleaning solution exiting the electrolysis cell 8 can be used to determine that the cleaning process has achieved the desired level, give a signal to the microprocessor 1 to convert to antimicrobial fluid production and thereby minimize the time that is devoted to cleaning.

The pumps 3, 5 can be of any type that can be run for an extended period of time without failure. Such pumps include peristaltic, gear, or any other positive displacement pump appropriate for relatively low viscosity fluids that can be controlled by the microprocessor 1. In a system where peristaltic pumps are used for fluid production and cleaning a maintenance protocol of lubrication and/or replacing worn tubing, for example the brine pump 5, during cleaning and tubing for a cleaning solution pump during HOCl solution production is easily instituted as the microprocessor 1 can provide an alarm when a period of time less than the anticipated lifetime of the tubing or lubrication cycle has occurred or where catastrophic loss of flow occurs. Where there are multiple pumps, one or more pumps can be employed for the control of the brine solution and one or more pumps can be employed for a cleaning solution. When one or more pumps are employed, one or more pump heads can be controlled by a single pump motor. For example, two peristaltic pump heads can be employed on a single motor, and can be 180 degrees out of phase to diminish pulsations in the fluid imposed by the pump head. Optionally, inline mixers can be employed at any point where two fluids are combined, for example, where the brine is introduced to the water. Inline mixtures can be static or active mixers. Flow of the water solution can be set using an inlet valve 12 controlled by the microprocessor 1. Flow indicators, for example 11, can be situated before and/or after the valve(s) 12, 15, 16, pump(s) 3, electrolysis cell 8 and exit of the system. Comparison of multiple flow indicators can be used by the microprocessor 1 to determine any breach in the system that can automatically stop the flow, locate the position of the breach and alarm an operator for initiation or repair. One or more three-way valves 12, 15, 16, a plurality of two-way valves, or any combination thereof can be controlled by the microprocessor 1 to direct the fluid passing through the system and collected depending on whether the production or cleaning fluid is within the system. Furthermore, these valves can be actuated such that any antimicrobial solution produced that displays pH or ORP outside of the prescribed parameters can be diverted from the outlet flow for collection or use of the antimicrobial fluid, where the diverted fluid can be collected with the cleaning solution, directed to a waste discharge, or even recycled into the electrolysis system for reprocessing. Generally, at antimicrobial fluid production startup, the fluid will be outside of the prescribed parameters and diverted from the product outlet. When antimicrobial fluid cannot be readily brought within the parameters within a short prescribed time period after cleaning, the microprocessor can alarm an operator for manual intervention.

Generally, the water supply 7 is free of sediments and can be free of salts other than NaCl. Hence, the system, as needed, can include one or more filters 17 and/or purification systems, such as a reverse osmosis (RO) unit, ion exchange columns, and/or absorbents. The rate of antimicrobial solution production can be as little as 50 L/hr when using a single small electrolysis cell 8 in the system, to 200 L/hr or more with a single larger electrolysis cell, to as much as 5,000 L/hr when multiple large electrolysis cells are employed in parallel. The novel system allows for high conversion of NaCl to HOCl, for example, with more than 700 ppm HOCl produced at a fluid production rate of 200 L/hr with a single cell, and more than 1,000 ppm HOCl produced at a fluid production rate of 100 L/hr with a single cell, depending upon the salt concentration employed.

In general, the system can be housed in one or a combination of two or more certified plastic or medical grade 316 SS enclosures. Generally, each enclosure is fitted with ventilation fans such that the interior of the system does not encounter a high level of a corrosive atmosphere or moisture. In one embodiment of the invention, the system is housed in two enclosures that can be easily shipped in two containers and readily stacked, electronically connected, and secured to each other where an enclosure containing the electronic components, including the controllers 14 and indicators 14, power supply 2, and microprocessor 1 is situated above an enclosure containing the cell(s) 8, pump(s) 5, 17, valves 12, 15, 16, probes 9, 10, and tubing for liquid handling. Tubing can be plastic, glass, or metal and can be flexible or inflexible. Appropriate tubing can be any that does not react with the HOCl comprising or cleaning solutions, as can be appreciated by one skilled in the art.

Embodiments of the invention are directed to a method of production of an antimicrobial solution comprising HOCl at a concentration in excess of 500 ppm at a rate in excess of 50 L/hr by use of the system described above. The method involves the introduction of brine 6 via a pump 5 into a flow of water that is directed into one or more electrolysis cells 8. The water is sediment free and low in non-NaCl salt concentration. The flow of water and the mixing with brine is detected by providing a signal to a microprocessor 1 that actuates valves 12 and/or pumps 3, 5 to achieve a desired NaCl concentration and ultimately a desired HOCl concentration. The salt solution is delivered into one or more electrolysis cells 8 that comprise end-caps, cylindrical electrodes and a porous ceramic membrane situated between the electrodes. The DC current applied across the electrodes is supplied by a digital power supply 2 that is controlled by the microprocessor 1 such that the voltage can float but the current is nearly constant. The power can be applied as a wave, for example, a square wave. In this manner the single fluid exiting the electrolysis cell 8 is about 6.5 in pH as read by an inline pH probe 10 situated in the effluent from the electrolysis cell 8 where software employed by the microprocessor 1 determines and executes appropriate modification of the flow rates and brine concentration to achieve a consistent solution comprising HOCl within the desired specifications. An ORP probe 9 is also included in the effluent stream where the signal from that probe is also included for the determination of brine concentration and flow parameters imposed by the microprocessor 1 on the system. The ORP output can be used to assess and assure that the cell 8 is mechanically sound during a production run. The microprocessor 1 can control the path of the effluent stream to assure that the effluents are directed to anolyte and catholyte storage containers 18 and 19 or a process stream where the solution is used, only when the desired pH, ORP, and current conditions are displayed in the effluent. In this manner, a solution comprising HOCl can be generated at a rate of 50 to about 1,000 L/hr with a HOCl concentration of 500 to 1,000 ppm. The system is designed to have the microprocessor 1 determine that cell performance has deteriorated, discontinue production and proceed with a cleaning regiment, where the microprocessor 1 diverts the cleaning effluent stream to an appropriate receiver 20. The microprocessor 1 can be used to determine that cleaning has been completed and restart the production of the solution comprising HOCl.

MATERIALS AND METHODS

Exemplary Electrolysis System

An exemplary electrolysis system contained in two compartments is shown schematically in FIG. 1, and includes: power supply 2, microprocessor 1, relays, safety breakers, filter 17 or other water purification device, pressure regulator, water valve (solenoid) 13, water flow controller 4, brine source 6, brine pump 5, cleaning solution 13, cleaning solution pump, 3-way selection valve 12, actuating pH control valve, electrolysis cell 8, ORP probe 9 and controller, ORP indicator 14, pH probe 10 and controller, pH indicator 14, cooling fans for both compartments, —3/8 inch OD and 1/4 inch OD flexible hose (3/8 inch OD used for flow to the reservoirs for Ultra-Lyte (anolyte) 18, catholyte 19 and drain 20, 1/4 inch OD used for brine feed), suction tubes for the brine pump 5 and cleaning pump, and brine tank 6 with a circulating pump 3 and float, and spare 5 micron filters.

Figure 2:
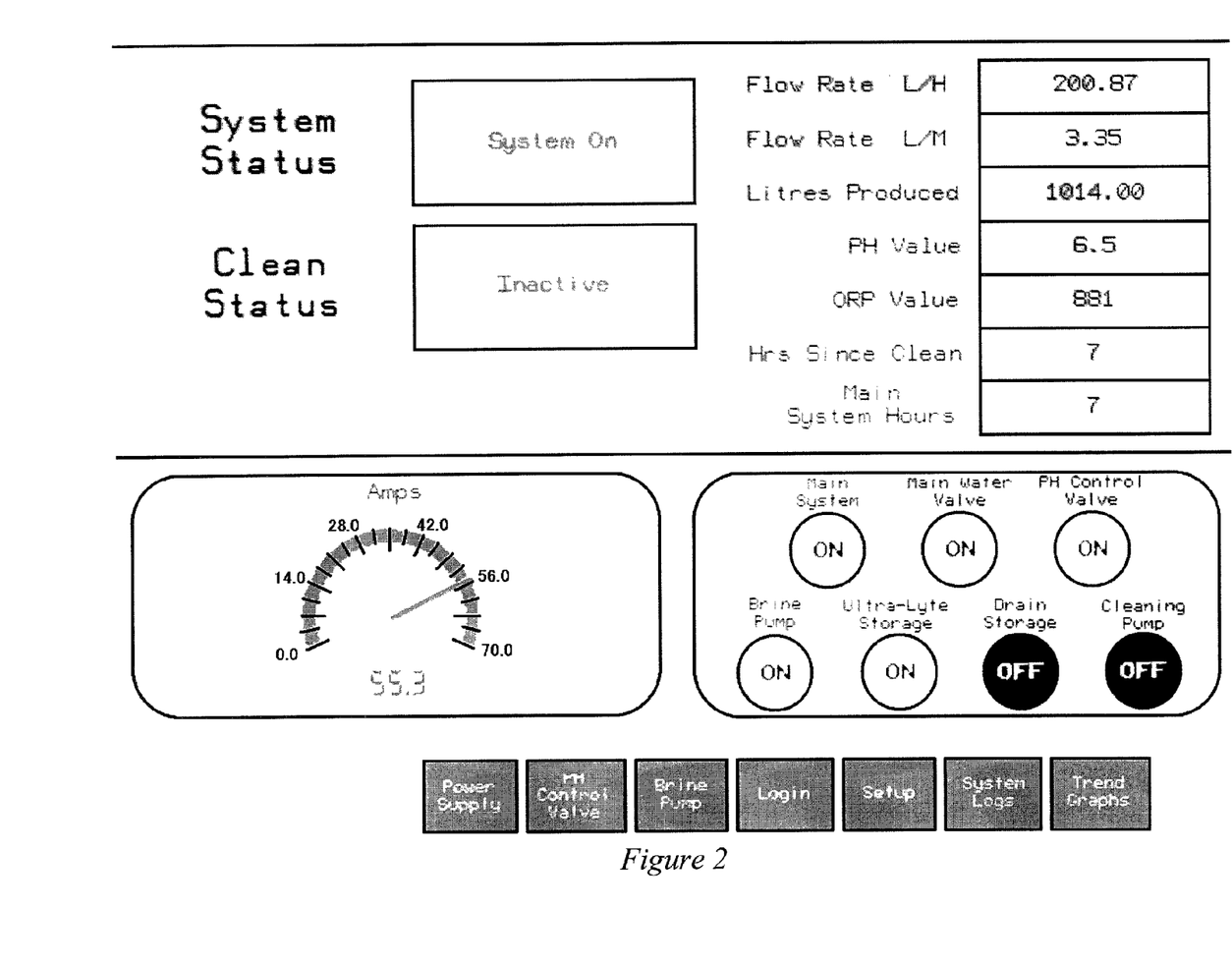
FIG. 2 is a representation of displayed real time settings and production values for an electrolysis system for the preparation of a solution comprising HOCl according to an embodiment of the invention where flow rates, pH and ORP values are displayed during microprocessor controlled production.
Figure 3:
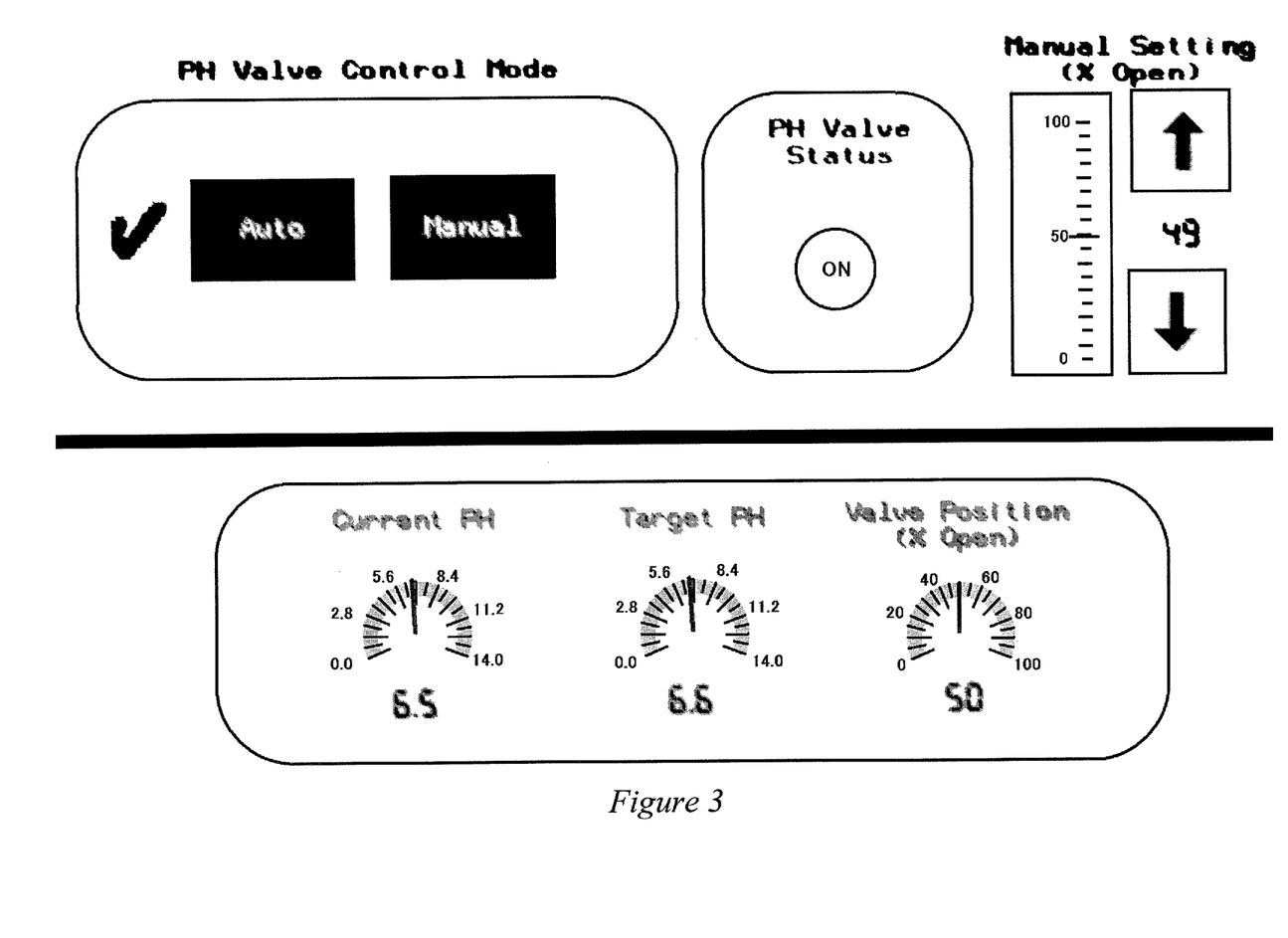
FIG. 3 is a representation of displayed real time settings and production values for an electrolysis system for the preparation of a solution comprising HOCl according to an embodiment of the invention where pH valve setting and target and observed pH in the system are displayed.
Figure 4:
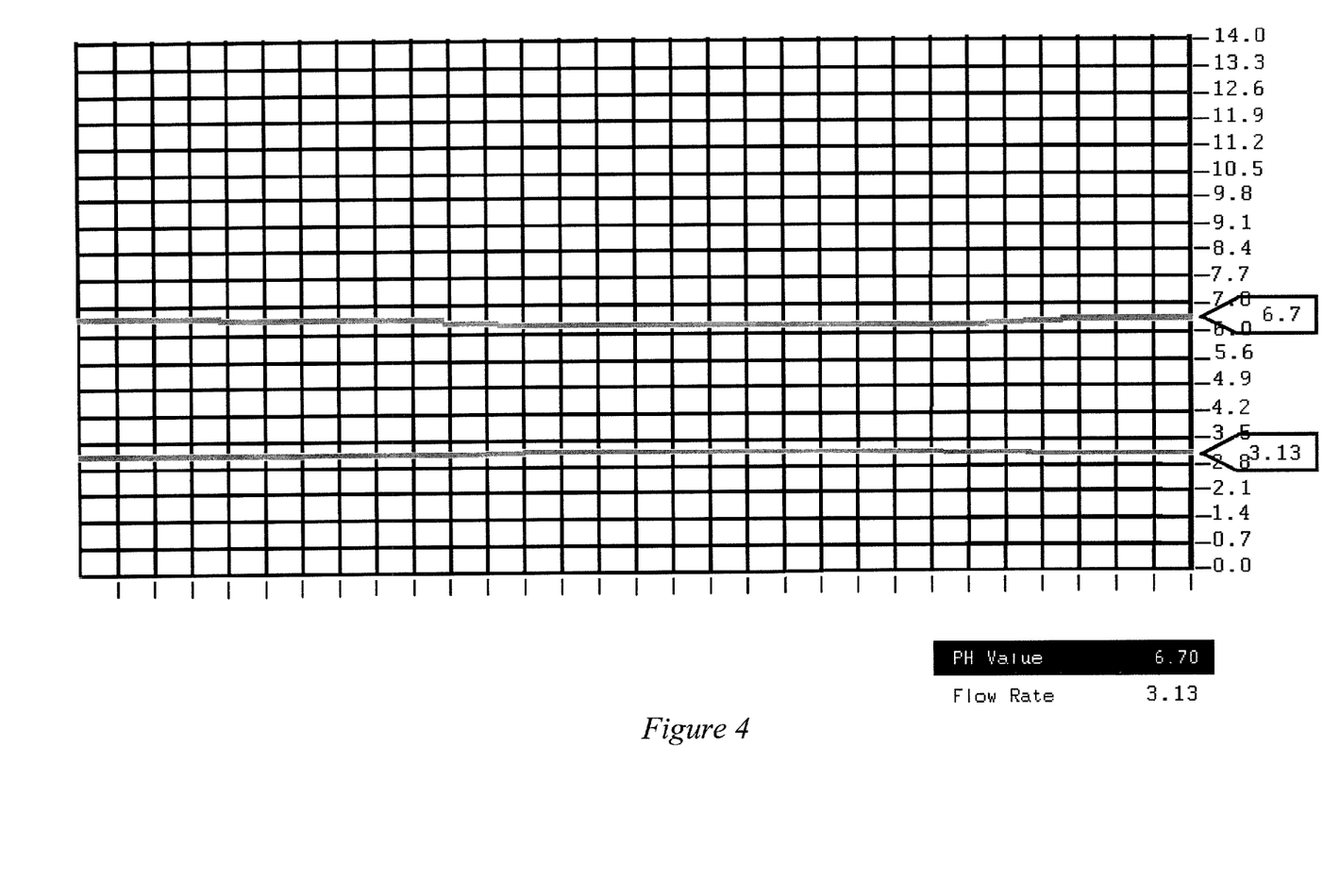
FIG. 4 is a representation of displayed real time of an electrolysis system for the preparation of a solution comprising HOCl according to an embodiment of the invention where plots of pH and flow rate during production are displayed along with the target (below plot) and instant (arrows on the right axis) values over a period of 10 minutes.

The following indicates how the illustrated exemplary system according to an embodiment of the invention functions. The software allows all the components to function together and synchronizes the process. FIGS. 2-4 show representations of data displayed on a microprocessor's touch screen when running the system according to an exemplary embodiment of the invention where: the instant amperage, flow rate, pH and ORD are indicated (FIG. 2); the pH target, pH instant value and a pH valve setting is displayed (FIG. 3); and a display of a plot of pH and flow over time with the instant values and the target values (FIG. 4), where the values over time can be stored shows the consistent controlled product available using the microprocessor control and controlled constant current available from the system according to an embodiment of the invention. To start, two options for the system to start production: (1) the timer can be set, for example, for 1 to 22 hours; or (2) install an external float in the anolyte storage tank 18 that shuts the system off as needed. When the system is in a startup mode, there is a 10 second time delay before the main solenoid opens to allow water through the system. The system runs software checks. Starting from the solenoid, water goes through the pressure regulator, reducing water pressure to 15-20 psi, and then passing the water through the 5 micron filter 17. The water passes through the flow control 4 which is preset by an operator to a proper flow rate. From the flow control 4 the water enters the flow meter 11 to measure constant flow and total flow which can be displayed on the touch screen 14. From the flow meter 11, water enters the electrolytic cell 8 and then flows to 3-way valves 15, 16, as programmed to direct liquid into the drain storage 20 after each startup and shut down until proper system parameters have been met, at which time the flow is directed to the anolyte storage tank 18. This ensures a consistent liquid inside the anolyte storage tank 18. The brine pump 5 and DC power to the electrolytic cell 8 are simultaneously started approximately half a minute after initial startup. This starts the electrolytic process to produce HOCl solution. Once the desired liquid is being produced, the 3-way valve 16 directs flow to the anolyte storage position. The 3-way valve 16 will change flow to the drain storage 20 whenever the machine goes outside the desired parameter range during the production mode. The desired range includes anything within set point of amps, brine feed percentage, water flow, pH readings, and ORP readings. As HOCl solution is produced, it enters the manifold containing the pH 10 and ORP 9 probes that send real time readings to the touch screen 14 showing the operator HOCl settings and values. The pH probe 10 signals the pH control valve via the microprocessor's 1 programmable logic controller (PLC), which, depending on the operator's pH setting, opens or closes valves proportionally to meet that operator's desired pH target. Whenever the system goes into shut down mode, either when the preset cycle of the timer is completed or when the storage tank is full, the 3-way valves 15, 16 turn to drain storage while the system remains in HOCl solution production mode to ensure the desired solution is being formed for reintroduction in the anolyte storage tank 18. Once the 3-way valve has verified proper valve positions, the system can go into a shut down mode, which turns off the power to the cell 8 and brine pump 5 and flushes the system with fresh water followed by cleaning out any residual brine in the lines and the cell 8. After shut down, cooling fans remain activated for 15 minutes to allow the system to properly cool off. The system is then deactivated until the storage tank needs to fill again or for an operator to reset the timer for the next production cycle.

The system is designed to clean on the schedule the operator presets in the PLC with the set cleaning time. The timer can be set to clean hourly or weekly. The system can be used for HOCl solution production for up to about 130 hours between cleaning cycles. The operator has the option to manually activate the cleaning cycle should he choose to override a preset cycle. Hydrochloric acid (HCl) or muriatic acid can be used for cleaning. Either acid should be less than 5% and diluted with RO water or distilled water. When the system needs to be cleaned, the system will switch the 3-way valve to drain storage position and go into shut down mode. The pH valve will completely close, ensuring total flow throughout the electrolytic cell. The system will flush with fresh water for 40 seconds, activate the cleaning pump for 2 minutes, let a 5% acid solution soak for 2 minutes, flush again with fresh water for 1.5 minutes, restart the cleaning pump for another 2 minutes, let the system soak for 7 minutes, then flush with fresh water for 4 minutes to remove all acid from the system. The system will automatically go into production mode as required by the storage tank or command from the PLC.

HOCl Solution Analysis Samples labeled UL-10, UL-11, UL-12, UL-13, UL-14, UL-15, UL-16, UL-17, UL-18, and UL-19 were examined for available chlorine and for pH assessment. The concentration of available chlorine in the test sample was determined by a colorimetric sodium thiosulfate titration method. Potassium iodide (KI) and sulfuric acid ($H_2SO_4$) were added to an aliquot of test sample with mixing and titrated with sodium thiosulfate and a starch indicator to a visible endpoint. The pH of each test sample was determined in triplicate using a calibrated pH probe capable of measuring pH to ±0.05. The hypochlorous acid concentration of each test sample was calculated using the average pH and the available chlorine as determined. Results are summarized in Tables 1-3, below.

Triplicate samples of each test sample were transferred to individual vessels and titrated. The weight of sample was determined by the following calculation:

$$\text{Weight of sample (in grams)} = \frac{(N \text{ of titrant}) \times (15 \text{ mL titrant}) \times (36 \text{ g Cl}^- /\text{Eq}) \times 1000}{(\text{Anticipated ppm of NaOCl solution to be titrated})}$$

where $N$ of titrant = Normality of the Sodium thiosulfate ($Na_2S_2O_3$).

The calculated amount of sample was transferred to three clean vessels. To each vessel was added 10.0 mL of 10% KI solution and 10.0 mL of 10% $H_2SO_4$ with mixing. A burette was filled with the titrant, 0.1003N Sodium thiosulfate. The titrant was added dropwise to the vessel with mixing. The titrant was added until a pale yellow color emerged. Once the pale yellow color was achieved, four drops of a starch indicator was added and mixed resulting in a dark purple and/or blackish colored solution. Titration was continued until a clear endpoint was achieved and the volume of titrant added was recorded. The average ppm value was determined for the triplicate samples. To calculate the available chlorine concentration (FAC):

$$\text{ppm available Cl} = \frac{(\text{mL titrant used}) \times (N \text{ of titrant}) \times (35.45 \text{ g Chlorine/Eq}) \times 1000}{(\text{actual sample weight in grams})}$$

The percent hypochlorous acid (HOCl) was calculated by the equation:

$$\% \text{ HOCl} = 100 \times [1 + K_i/(H^+)]^{-1}$$

where: $K_i$ is the dissociation constant of HOCl at 20° C. or $2.621 \times 10^{-8}$ mol/L and $(H^+)$ is the negative $\log_{10}$ of the average pH value per sample.

The percent of available HOCl was calculated as:

$$\% \text{ Available HOCl} = \frac{\% FAC \times \% \text{ HOCl}}{100}$$

The pH measurements were conducted in triplicate at room temperature using a temperature compensating probe and a pH meter capable of measuring pH to ±0.05. At least two NIST traceable reference buffers, of pH 4.00, 7.00 and 10.00, were used to calibrate the pH meter prior to each sample analysis.

TABLE 1 pH of Sample Solutions

| Sample | Run | pH | Average pH |
|---|---|---|---|
| UL-10 | 1 | 6.16 | 6.17 |
| | 2 | 6.16 | |
| | 3 | 6.19 | |
| UL-11 | 1 | 6.22 | 6.23 |
| | 2 | 6.22 | |
| | 3 | 6.26 | |
| UL-12 | 1 | 6.23 | 6.24 |
| | 2 | 6.24 | |
| | 3 | 6.24 | |
| UL-13 | 1 | 6.24 | 6.24 |
| | 2 | 6.23 | |
| | 3 | 6.24 | |
| UL-14 | 1 | 6.28 | 6.29 |
| | 2 | 6.28 | |
| | 3 | 6.31 | |
| UL-15 | 1 | 6.39 | 6.38 |
| | 2 | 6.37 | |
| | 3 | 6.38 | |
| UL-16 | 1 | 6.34 | 6.36 |
| | 2 | 6.37 | |
| | 3 | 6.37 | |
| UL-17 | 1 | 6.34 | 6.35 |
| | 2 | 6.36 | |
| | 3 | 6.36 | |
| UL-18 | 1 | 6.41 | 6.40 |
| | 2 | 6.39 | |
| | 3 | 6.41 | |
| UL-19 | 1 | 6.33 | 6.35 |
| | 2 | 6.35 | |
| | 3 | 6.36 | |

TABLE 2

FAC Titration Results

| Sample | Run | Sample Mass (g) | Vol. Titrant (mL) | FAC (ppm) | Average FAC |
|---|---|---|---|---|---|
| UL-10 | 1 | 41.63 | 7.6 | 649 | 647 |
| | 2 | 40.77 | 7.4 | 645 | |
| UL-15 | 1 | 108.25 | 16.8 | 552 | 546 |
| | 2 | 99.84 | 15.3 | 545 | |
| | 3 | 99.73 | 15.2 | 542 | |
| UL-16 | 1 | 99.99 | 15.2 | 541 | 539 |
| | 2 | 100.09 | 15.3 | 544 | |
| | 3 | 99.07 | 14.8 | 531 | |
| UL-17 | 1 | 99.53 | 15.1 | 539 | 539 |
| | 2 | 99.82 | 15.2 | 541 | |
| | 3 | 99.84 | 15.1 | 538 | |
| UL-18 | 1 | 99.73 | 14.7 | 524 | 526 |
| | 2 | 99.96 | 14.8 | 526 | |
| | 3 | 99.24 | 14.7 | 527 | |
| UL-19 | 1 | 100.06 | 15.3 | 544 | 544 |
| | 2 | 100.26 | 15.3 | 543 | |
| | 3 | 100.02 | 15.3 | 544 | |

TABLE 3

Calculated HOCl in ppm

| Sample | FAC (ppm) | pH | % HOCl of FAC | HOCl (ppm) |
|---|---|---|---|---|
| UL-15 | 546 | 6.38 | 94.1 | 514 |
| UL-16 | 539 | 6.36 | 94.3 | 508 |
| UL-17 | 539 | 6.35 | 94.5 | 509 |
| UL-18 | 526 | 6.40 | 93.8 | 493 |
| UL-19 | 544 | 6.35 | 94.5 | 514 |

Efficacy of Solutions after 60 Days.

Ten (10.0) mL aliquots of a 60 day old test sample were transferred to sterile 25×150 mm tubes, placed in a 20±1° C. water bath and allowed to equilibrate for ≥10 minutes. Test Organisms *Staphylococcus aureus* (ATCC 6538) and *Salmonella enterica* (ATCC 10708) were examined where from a stock slant, an initial tube of culture broth was inoculated. From this initial broth suspension, a minimum of three daily transfers were performed on consecutive days prior to use in testing. For each test organism, the appropriate growth medium was sub cultured using a daily transfer (more than 3, but less than 30 transfers) of the test organism. A 48-54 hour broth culture incubated at 35-37° C. was prepared. The test cultures were thoroughly mixed and allowed to stand for ≥10 minutes prior to use.

A 3.3 mL aliquot of a fetal bovine serum (FBS) was added to 62.7 mL of each broth culture to yield a 5% fetal bovine serum soil load.

Sterile penicylinders were immersed for 15 minutes in a 48-54 hour old broth culture of the test organism, at a ratio of 1 carrier per 1.0 mL broth. The exposed penicylinders were dried on filter paper in a sterile Petri dish at 35-37° C. for 40 minutes at 39% relative humidity.

Sixty contaminated and dried carriers were individually transferred by hook needle at staggered intervals to individual tubes containing 10.0 mL of the test samples and exposed for 10 minutes at 20±1° C. Following exposure, each medicated carrier was transferred by hook needle at identical staggered intervals to 10 mL of Letheen Broth+ 0.2% Sodium Thiosulfate. The neutralized subculture tubes and plates were incubated for 48±4 hours at 35-37° C. and visually examined for the presence or absence of growth.

Representative neutralized subcultures showing growth were sub cultured on appropriate agar to confirm or rule out the presence of the test organism.

Test controls included that of purity, organic soil sterility, carrier sterility, normalized subculture sterility, viability, neutralization confirmation, and carrier population control. Purity Control was conducted by a "streak plate for isolation" performed on the organism culture examined following incubation to confirm the presence of a pure culture. The acceptance criterion for this study control is a pure culture demonstrating colony morphology typical of the test organism. Organic Soil Sterility Control was conducted on the serum used for soil load involved culturing, incubating, and visually examining for lack of growth. The acceptance criterion for this study control is lack of growth. Carrier Sterility Control was conducted by adding a representative uninoculated carrier to the neutralizing subculture medium. The subculture medium containing the carrier was incubated and examined for growth. The acceptance criterion for this study control is lack of growth. Neutralizing Subculture Medium Sterility Control involved incubating and visually examining a representative sample of uninoculated neutralizing subculture medium. The acceptance criterion for this study control is lack of growth. Viability Control was carried out where a representative inoculated carrier was added to the subculture medium. The subculture medium containing the carrier was incubated and visually examined for growth. The acceptance criterion for this study control is growth. Neutralization Confirmation Control involved neutralization of the test substance, confirmed by exposing sterile carriers (representing not less than 10% of the total number of test carriers) to the test substance and transferring to subculture tubes containing 10 mL of neutralizing subculture medium. The subculture tubes containing the exposed carriers were inoculated with ≤100 colony forming units (CFU) of the test organism, incubated under test conditions and visually examined for the presence of growth. Control was performed with multiple replicates using different dilutions of the test organism. A standardized spread plate procedure was run concurrently in order to enumerate the number of CFU actually added. Control results are reported using data from the most appropriate dilution. The acceptance criterion for this study control is growth after inoculation with ≤100 CFU. Carrier Population Control involved adding inoculated carriers at a ratio of 1 carrier to 10 mL neutralizing broth and vortex mixing. Appropriate serial ten-fold dilutions were prepared and aliquots were spread plated on agar plate medium, and incubated. Following incubation, the resulting colonies were enumerated and the CFU/carrier calculated. The acceptance criterion for this study control is a minimum of 1.0×10⁴ CFU/carrier. Carrier Population was calculated as:

$$CFU/\text{carrier} = \frac{(\text{avg number colonies/plate @ dilution}) \times (\text{dilution factor}) \times (\text{volume neutralizer})}{(\text{number of carriers tested}) \times (\text{volume plated})}$$

All data measurements/controls including the culture purity, viability, organic soil sterility, neutralizing subculture medium sterility, carrier sterility, neutralization confirmation, and carrier population were within acceptance criteria. Control and Neutralization Results are given in Tables 4-6, below. Test Results are given in Table 7, below.

TABLE 4

Control Results

| Control Type | Staphylococcus aureus (ATCC 6538) | Salmonella enterica (ATCC 10708) |
|---|---|---|
| Purity Control | Pure | Pure |
| Viability Control | Growth | Growth |
| Organic Soil Sterility Control | No Growth | |
| Neutralizing Subculture Medium Sterility Control | No Growth | |
| Carrier Sterility Control | No Growth | |

TABLE 5

Carrier Population Control Results

| Test Organism | Result |
|---|---|
| Staphylococcus aureus (ATCC 6538) | 8.6 × 10⁶ CFU/carrier |
| Salmonella enterica (ATCC 10708) | 5.0 × 10⁶ CFU/carrier |

TABLE 6

Neutralization Confirmation Control Results

| Test Sample | Test Organism | Average Inoculum (CFU/mL) | Number of Subculture Tubes Tested | Positive |
|---|---|---|---|---|
| UL-01 aged 61 days | Staphylococcus aureus (ATCC 6538) | 5 | 6 | 6 |
| | Salmonella enterica (ATCC 10708) | 26 | 6 | 6 |

TABLE 7

Test Results

| Test Sample | Test Organism | Number of Carriers Exposed | Showing Growth |
|---|---|---|---|
| UL-01 aged 61 days | Staphylococcus aureus (ATCC 6538) | 60 | 1 |
| | Salmonella enterica (ATCC 10708) | 60 | 0 |

The EPA efficacy performance requirements for label claims state that the test substance must kill the microorganism on 59 out of the 60 inoculated carriers. Health Canada performance requirements for label claims state that the test substance must kill the microorganism on 58 out of the 60 inoculated carriers.

Stability of solutions after 6 months

The available chlorine concentration (FAC) was calculated by the equation:

$$FAC(mg/L) = A \times N \times 1000/V$$

where A is the volume of titrant for sample (mL) N is the normality of FAS (in Cl/eq)=0.1 mg Cl/mL and V is the volume of Sample (mL).

The test substance was formulated at 0.005% Free Available Chlorine (FAC). The Confidential Statement of Formula (CSF) submitted to the EPA has defined upper limits of +20% and lower limits of −10%. Therefore the allowable levels of FAC are an upper limit of 0.0060% and a lower limit of 0.0045%. Table 8 gives the results of pH determinations and FAC for samples analyzed in triplicate over a 6 month period. Sample #1 was analyzed at the start of the study, and determined to have an average Free Available Chlorine level of 0.0059% and a pH of 6.23. The test substance was a clear colorless solution. Sample #2 was analyzed after 3 months and determined to have an average Free Available Chlorine level of 0.0047% and a pH of 5.06. The test substance is a clear colorless solution. Sample #4 was analyzed after 6 months and determined to have an average Free Available Chlorine level of 0.0045% and a pH of 5.11. The test substance is a clear colorless solution. Sample #5 was analyzed after 6 months and determined to have an average Free Available Chlorine level of 0.0045% and a pH of 5.47. The test substance is a clear colorless solution.

TABLE 8

Six Month Test Results

| Date | Sample ID | Run | pH | % FAC | Average % FAC |
|---|---|---|---|---|---|
| Aug. 20, 2010 | #1 | 1 | 6.23 | 0.0059 | 0.0059 |
|  |  | 2 |  | 0.0058 |  |
|  |  | 3 |  | 0.0058 |  |
| Nov. 22, 2010 | #2 | 1 | 5.06 | 0.0048 | 0.0047 |
|  |  | 2 |  | 0.0047 |  |
|  |  | 3 |  | 0.0047 |  |
| Feb. 18, 2011 | #4 | 1 | 5.11 | 0.0045 | 0.0045 |
|  |  | 2 |  | 0.0045 |  |
|  |  | 3 |  | 0.0045 |  |
| Feb. 18, 2011 | #5 | 1 | 5.47 | 0.0045 | 0.0045 |
|  |  | 2 |  | 0.0045 |  |
|  |  | 3 |  | 0.0045 |  |

The FAC Level dropped from a high of 0.0059% at the beginning of the study to a concentration of 0.0045% after 6-months. This reduction is within the limits defined in the CSF. The test substance remained a clear colorless solution throughout the study. Examination of the HDPE storage container at the 6-month interval revealed no visible signs of degradation or color staining. No problems were encountered during the course of the study that may have adversely affected the quality or integrity of the data.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An improved sealed electrolysis cell assembly comprising:
    an anode tube exterior to and concentric with a cathode tube, wherein the anode tube is titanium and has an interior surface catalytic coating consisting of a mixture of ruthenium, palladium, and iridium oxides;
    a ceramic membrane tube situated between the anode tube and the cathode tube, wherein the ceramic membrane tube is an injection molded alumina membrane tube;
    two insulating end pieces, each of the insulating end pieces comprising three concentric seats with diameters for positioning the anode tube, the ceramic membrane tube, and the cathode tube;
    at least one seal forming features in the vicinity of each of the seats, wherein upon sealing the anode tube, the ceramic membrane tube, and the cathode tube forms an anode chamber and a cathode chamber separated by the ceramic membrane tube;
    an anion chamber inlet in one of the insulating end pieces and an anode chamber outlet in the other the insulating end pieces and a cathode chamber inlet in one of the insulating end pieces and a cathode chamber outlet in the other insulating end pieces; and
    a cathode tap on the cathode tube and an anode tap welded to the anode tube, and wherein the anode tap has a surface area of 1.5 percent to 5 percent of the external surface area of the anode tube.

2. An antimicrobial solution comprising an HOCl generating and storage system, comprising:
    a source of sediment free water;
    a flow controller;
    a reservoir containing an agitator and a source of brine solution comprising NaCl or other alkali metal chloride;
    a first pump, having a first inlet connected to the source of brine to deliver the brine through a first outlet into a first conduit where the sediment free water and the brine form a chloride solution;
    a microprocessor having software to accept multiple input signals and generate multiple output signals wherein at least one of the input signals is provided by at least one user interfacing device;
    a source of a cleaning solution, wherein the cleaning solution comprises HCl;
    a second pump having a second inlet connected to a source of the cleaning solution to deliver the cleaning solution through a second outlet into the first conduit;
    at least one valve to selectively direct flow to one of a plurality of effluent outlets;
    at least one means to selectively deliver the NaCl solution or the cleaning solution into the first conduit, wherein the means to selectively deliver comprises one or more 3-way valves, a plurality of two way valves or one or more switches to selectively power the first pump or the second pump;
    a power supply;
    at least one sealed electrolysis cell assembly according to claim 1, wherein a solution comprising HOCl is discharged from the anode chamber outlet into a second conduit;
    an inline pH probe in the second conduit containing and situated downstream and proximal to the electrolysis cell having a first electrical connection providing a first input signal to the microprocessor;
    an inline oxidation/reduction potential (ORP) probe in the second conduit situated downstream and proximal to the electrolysis cell having a second electrical connection providing a second input signal to the microprocessor, the microprocessor is configured for determining and providing: a first output signal through a third electrical connection to the power supply; and a second output signal through a fourth electrical connection to the first pump to set a concentration of the NaCl solution and a third output signal through a fifth electrical connection to the means to selectively deliver of the brine solution and the cleaning solution, and wherein the microprocessor is programmed to provide the third output signal to deliver the cleaning solution;
    a flow indicator for providing a third input signal through a sixth electrical connection to the microprocessor for determination of an output signal provided through a seventh electrical connection to the flow controller; and an anolyte storage tank connected to one of the effluent outlets and containing the solution comprising HOCl.

3. The system of claim 2, wherein the power supply has an AC input of 208 to 220 V and a DC output of up to 100 A and up to 100 V to the electrolysis cell.

4. The system of claim 2, wherein the user interfacing device is a keyboard or a touch screen and wherein the interfacing device is local or remote to the microprocessor.

5. The system of claim 2, further comprising at least one output device, wherein the microprocessor outputs a signal to be observed by an operator and/or recorded on a recording medium.

6. The system of claim 5, wherein the output device comprises a display screen and/or a printer.

7. The system of claim 2, further comprising a storage device wherein the input and output history and production and cleaning set points are stored.

8. The system of claim 7, wherein the storage device is a magnetic, optical, or flash storage device.

9. The system of claim 2, wherein the system generates the solution comprising HOCl at a rate of 50 to 5,000 L/hour.

10. The system of claim 2, further comprising a second flow indicator to deliver a fourth input signal through an eighth electrical connection to the microprocessor.

11. The system of claim 2, wherein the means to selectively deliver further comprises at least one 3-way valve or a plurality of valves.

12. The improved sealed electrolysis cell assembly of claim 1, wherein the injection molded alumina membrane tube comprising 85 to 90% alumina and 7 to 9% silica.

13. The improved sealed electrolysis cell assembly of claim 1, wherein the injection molded alumina membrane tube has 0.3 μm pores and a tube thickness of 5 to 7 mm with variance in tube thickness of 2 percent or less.

14. The system of claim 2, wherein the concentration of HOCl in the solution comprising HOCl is 1000 to 1400 ppm.

* * * * *

UNITED STATES PATENT AND TRADEMARK OFFICE
CERTIFICATE OF CORRECTION

| | |
|---|---|
| PATENT NO. | : 9,777,383 B2 |
| APPLICATION NO. | : 15/162076 |
| DATED | : October 3, 2017 |
| INVENTOR(S) | : Duke van Kalken and Nathan Waldner |

It is certified that error appears in the above-identified patent and that said Letters Patent is hereby corrected as shown below:

In the Specification

<u>Column 6,</u>
Line 43, "data storage anchor" should read --data storage and/or--.

Signed and Sealed this
Twenty-second Day of May, 2018

Andrei Iancu
*Director of the United States Patent and Trademark Office*